(12) United States Patent
Iscovich et al.

(10) Patent No.: US 9,487,557 B2
(45) Date of Patent: Nov. 8, 2016

(54) PEPTIDES FOR MANAGEMENT OF LACTATION

(71) Applicant: MILEUTIS LTD., Gan Yavne (IL)

(72) Inventors: Jose Mario Iscovich, Gan Yavne (IL); Javier Iscovich, Karmei Yosef (IN)

(73) Assignee: MILEUTIS LTD., Gan Yavne (IL)

(*) Notice: Subject to any disclaimer, the term of this patent is extended or adjusted under 35 U.S.C. 154(b) by 0 days.

(21) Appl. No.: 14/384,395

(22) PCT Filed: Mar. 8, 2013

(86) PCT No.: PCT/IL2013/050214
§ 371 (c)(1),
(2) Date: Sep. 11, 2014

(87) PCT Pub. No.: WO2013/140388
PCT Pub. Date: Sep. 26, 2013

(65) Prior Publication Data
US 2015/0093400 A1 Apr. 2, 2015

Related U.S. Application Data

(60) Provisional application No. 61/612,410, filed on Mar. 19, 2012.

(51) Int. Cl.
| | | |
|---|---|---|
| C07K 1/00 | (2006.01) | |
| C07K 5/00 | (2006.01) | |
| C07K 7/06 | (2006.01) | |
| A61K 38/07 | (2006.01) | |
| A61K 38/08 | (2006.01) | |
| C07K 5/11 | (2006.01) | |
| C07K 14/47 | (2006.01) | |
| A61K 45/06 | (2006.01) | |
| A61K 38/17 | (2006.01) | |

(52) U.S. Cl.
CPC ............... *C07K 7/06* (2013.01); *A61K 38/07* (2013.01); *A61K 38/08* (2013.01); *A61K 45/06* (2013.01); *C07K 5/1019* (2013.01); *C07K 14/4732* (2013.01); *A61K 38/1709* (2013.01)

(58) Field of Classification Search
CPC ...................................................... C07K 7/06
See application file for complete search history.

(56) References Cited

U.S. PATENT DOCUMENTS

| 6,391,849 | B1 | 5/2002 | Shamay | |
|---|---|---|---|---|
| 7,968,513 | B2 | 6/2011 | Iscovich | |
| 2005/0220801 | A1* | 10/2005 | Otani | A23L 1/3053 424/185.1 |
| 2009/0092582 | A1* | 4/2009 | Bogin et al. | 424/85.5 |

FOREIGN PATENT DOCUMENTS

| EP | 1375513 | 1/2004 |
|---|---|---|
| WO | 2006/117784 | 11/2006 |

OTHER PUBLICATIONS

Greenberg et al (Journal of Biological Chemistry vol. 259, No. 8, pp. 5132-5138, 1984).*
Samaraweera et al "Egg Yolk Phosvitin and Functional Phosphopeptides—Review" Journal of Food Science. 76 (7)R143-R150 (2011).
Young et al "Identification of Hen Egg Yolk-Derived Phosvitin Phosphopeptides and Their Effects on gene Expression Profiling against Oxidative Stress-Induced Caco-2 Cells" Journal of Agriculture and Food Chemistry. 59 (17)9207-9218 (Aug. 2011) abstract.
Bitter et al., (1987) Expression and secretion vectors for yeast. Methods Enzymol 153: 516-44.
Capuco and Akers (1999) Mammary involution in dairy anaimas. J Mammary Gland Biol Neoplasia 4(2): 137-44.
Fields and Noble (1990) Solid phase peptide synthesis utilizing 9-fluorenylmethoxycarbonyl amino acids. Int J Pept Protein Res 35(3): 161-214.
Fitzgerald (1998) Potential uses of caseinophosphopeptides. Int Dairy 8(5-6): 451-457.
GenBank Acc # JN0547, Bouniol C, Brignon C, Mahe MF and Printz C, Oct. 15, 1999 http://www.ncbi.nlm.nih.gov/protein/JN0547?report=penpept.
GenBank Acc # KASHS2, Boisnard M and Petrissant G, Jun. 22, 1999 http://www.ncbi.nlm.nih.gov/protein/KASHS2?report=penpept.
Hata et al., (1998) Identification of a phosphopeptide in bovine alpha s1-casein digest as a factor influencing proliferation and immunoglobulin production in lymphocyte cultures. J Dairy Res 65(4)1569-78.
Hata et al., (1999) Immunostimulatory action of a commercially available casein phosphopeptide preparation, CPP-III, in cell cultures. Milchwissenschaft 54(1): 3-7.
Li et al., (1997) Mammary-derived signals activate programmed cell death during the first stage of mammary gland involution. Proc Natl Acad Sci U S A 94(7): 3425-30.
Marti et al., (1997) Milk accumulation triggers apoptosis of mammary epithelial cells. Eur J C Biol 73(2): 158-65.
Meggio et al., (1991) A synthetic beta-casein phosphopeticle and analogues as model substrates for casein kinase-1, a ubiquitous, phosphate directed protein kinase. FEBS Lett 283(2): 303-6.
Merrifield (1963) Solid phase peptide synthesis. I. The synthesis of a tetrapeptide, J Am Chem Soc 85: 2149-2154.
Oliver and Sordillo (1989) Approaches to the manipulation of mammary involution. J Dairy Sci 72(6): 1647-64.
Perich (1997) Synthesis of phosphopeptides using modern chemical approaches. Methods Enzymol 289: 245-66.
Quarrie et al., (1994) Local regulation of mammary apoptosis in the lactating goat. Biochem Soc Trans 22(2): 178S.
Shamay et al., (2002) Casein-derived phosphopeptides disrupt tight junction integrity, and precipitously dry up milk secretion in goats. Life Sci 70(23): 2707-19.

(Continued)

*Primary Examiner* — Albert Navarro
(74) *Attorney, Agent, or Firm* — Browdy and Neimark, PPLC

(57) ABSTRACT

The present invention provides novel short peptides that are highly effective in inducing involution in a mammary gland of a lactating mammal and cessation of milk production by the gland. The invention further provides pharmaceutical composition comprising the peptides and methods of use thereof including for treating microbial infection in a mammary gland.

20 Claims, No Drawings

(56) References Cited

OTHER PUBLICATIONS

Shamay et al., (2003) Infusions of casein hydrolyzates into the mammary gland disrupt tight junction integrity and induce involution in cows. J Dairy Sci 86(4): 1250-8.

Slianikove et al., (2000) Stress down regulates milk yield in cows by plasmin induced beta-casein product that blocks K + channels on the apical membranes. Life Sci 67(18): 2201-12.

Studier et al., (1990) Use of T7 RNA polymerase, to direct expression of cloned genes. Methods Enzymol 185: 60-89.

Wilde et al., (1999) Control of milk secretion and apoptosis during mammary involution. J Mammary Gland Biol Neoplasia 4(2): 129-36.

GenPept Accession No. JN0547 for alpha-s2-casein precursor—goat, downloaded from the NCBI database on Apr. 12, 2016.

GenPept Accession No. KASHS2 for alpha-s2-casein precursor—sheep, downloaded from the NCBI database on Apr. 12, 2016.

* cited by examiner

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: X represents 0-2 amino acids; at least one of X
      at position 1 or 5 is positively charged amino acids.
<220> FEATURE:
<221> NAME/KEY: MISC_FEATURE
<222> LOCATION: (2)..(4)
<223> OTHER INFORMATION: Modified by phosphoric acid
<220> FEATURE:
<221> NAME/KEY: Xaa
<222> LOCATION: (5)..(5)
<223> OTHER INFORMATION: X represents 0-2 amino acids; at least one of X
      at position 1 or 5 is positively charged amino acids.
```

```
<400> SEQUENCE: 1

Xaa Ser Ser Ser Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(5)
<220> FEATURE:
<221> NAME/KEY: MISC_FEATURE
<222> LOCATION: (3)..(5)
<223> OTHER INFORMATION: Modified by phosphoric acid

<400> SEQUENCE: 2

Lys Lys Ser Ser Ser
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(5)
<223> OTHER INFORMATION: Modified by phosphoric acid

<400> SEQUENCE: 3

Lys Lys Ser Ser Ser Lys
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(5)
<223> OTHER INFORMATION: Modified by phosphoric acid

<400> SEQUENCE: 4

Lys Lys Ser Ser Ser Lys Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(4)
<223> OTHER INFORMATION: Modified by phosphoric acid

<400> SEQUENCE: 5

Lys Ser Ser Ser Lys Lys
1               5

<210> SEQ ID NO 6
```

```
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(4)
<223> OTHER INFORMATION: Modified by phosphoric acid

<400> SEQUENCE: 6

Lys Ser Ser Ser Lys
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(4)
<223> OTHER INFORMATION: Modified by phosphoric acid

<400> SEQUENCE: 7

Lys Ser Ser Ser
1

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: Modified by phosphoric acid

<400> SEQUENCE: 8

Ser Ser Ser Lys Lys
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: Modified by phosphoric acid

<400> SEQUENCE: 9

Ser Ser Ser Lys
1

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Modified by phosphoric acid
<220> FEATURE:
<221> NAME/KEY: MISC_FEATURE
```

```
<222> LOCATION: (5)..(7)
<223> OTHER INFORMATION: Modified by phosphoric acid
<220> FEATURE:
<221> NAME/KEY: Xaa
<222> LOCATION: (8)..(8)
<223> OTHER INFORMATION: Amid

<400> SEQUENCE: 10

Lys Lys Ser Leu Ser Ser Ser Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Amid

<400> SEQUENCE: 11

Lys Lys Ser Leu Ser Ser Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(5)
<223> OTHER INFORMATION: Modified by phosphoric acid
<220> FEATURE:
<221> NAME/KEY: Xaa
<222> LOCATION: (6)..(6)
<223> OTHER INFORMATION: Amid

<400> SEQUENCE: 12

Lys Lys Ser Ser Ser Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Amid

<400> SEQUENCE: 13

Lys Lys Ser Ser Ser Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Modified by phosphoric acid
<220> FEATURE:
```

```
<221> NAME/KEY: Xaa
<222> LOCATION: (5)..(5)
<223> OTHER INFORMATION: Amid

<400> SEQUENCE: 14

Lys Lys Ser Ser Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: aMID

<400> SEQUENCE: 15

Lys Lys Ser Ser Xaa
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Modified by phosphoric acid
<220> FEATURE:
<221> NAME/KEY: MISC_FEATURE
<222> LOCATION: (4)..(6)
<223> OTHER INFORMATION: Modified by phosphoric acid
<220> FEATURE:
<221> NAME/KEY: Xaa
<222> LOCATION: (9)..(9)
<223> OTHER INFORMATION: Amid

<400> SEQUENCE: 16

Glu Ser Leu Ser Ser Ser Glu Glu Xaa
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (9)..(9)
<223> OTHER INFORMATION: Amid

<400> SEQUENCE: 17

Glu Ser Leu Ser Ser Ser Glu Glu Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(4)
<223> OTHER INFORMATION: Modified by phosphoric acid
```

```
<220> FEATURE:
<221> NAME/KEY: Xaa
<222> LOCATION: (7)..(7)
<223> OTHER INFORMATION: Amid

<400> SEQUENCE: 18

Lys Ser Ser Ser Glu Glu Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Amid

<400> SEQUENCE: 19

Lys Ser Ser Ser Glu Glu Xaa
1               5
```

PEPTIDES FOR MANAGEMENT OF LACTATION

FIELD OF THE INVENTION

The present invention relates to the field of mammary gland lactation. Particularly, the present invention provides novel peptides for efficient and rapid disruption of lactation and for treating mastitis.

BACKGROUND OF THE INVENTION

Cessation of milk removal leads to changes in the mammary secretion and to initiation of the process of active mammary involution. This process comprises an extensive and highly ordered sequence of changes in tissue and milk composition, which occur during the transition between the lactating and the non-lactating states. The initial stage of mammary involution is triggered by local stimuli that initiate apoptosis, but involution can be reversed by reinitiating milk removal (Capuco and Akers, 1999. J. Mammary Gland Biol. Neoplasia 4:137-144; Wilde et al., 1999. J. Mammary Gland Biol. Neoplasia 4:129-136). This local control can cause involution when milk stasis is induced in individual glands, as was observed in lactating goats following unilateral cessation of milking (Quarrie et al., 1994. Biochem. Soc. Trans. 22:178 S), or in lactating mice following teat sealing (Li et al., 1997. Proc. Natl. Acad. Sci. U.S.A. 94: 3425-3430; Marti et al., 1997. Eur. J. Cell. Biol. 73:158-165).

The further stage of involution is persistent, and milk removal cannot cause resumption of milk secretion (Capuco and Akers, 1999. ibid; Wilde et al., 1999. ibid). Reversal of the persistent state of involution can occur only in a subsequent lactating period after giving birth. This after-parturition stage is characterized by activation of proteases that destroy the lobular-alveolar structure of the gland by degrading the extracellular matrix and basement membrane, as well as by massive loss of alveolar cells.

In the modern dairy industry, lactating animals in herds go through controlled cycles of milking and pregnancy, as such regimes contribute to a significant increase in milk production. In current management of dairy herds, for example cows and goats, there is a significant overlap between lactation and pregnancy, wherein a "dry period" is imposed between 35 to 75 days prior to parturition by cessation of milking. This regime is set to compromise between the need to induce involution, a necessary process for subsequent healthy lactating period, and the requirement for high milk production all year long.

Breastfeeding, or nursing, has been identified as the ideal method of feeding and nurturing infants and is considered a primary factor in achieving optimal infant and child health, growth, and development. Epidemiologic research shows that human milk and breastfeeding of infants significantly decreases the risk for or severity of a large number of acute and chronic diseases, and there are also a number of studies that indicate possible health benefits for the nursing mothers.

With these health benefits, as well as social and economic advantages, the American Academy of Pediatrics and the World Health Organization (World Health Organization. (2003). Global strategy for infant and young child feeding. Geneva, Switzerland: World Health Organization and UNICEF. ISBNO. 9241562218) has issued a policy statement that recommends breastfeeding exclusively for the first six months, then gradually introducing solid foods and continuing to breastfeed for at least six more months and after that for as long as mutually desired. In normal breastfeeding practices, weaning an infant from breastfeeding to another food source such as solid food, formula or fruit juices is a gradual process. As the infant's diet incorporates other food sources, the mother continues to nurse but either decreases the amount of time at each feeding, decreases the number of breast feedings each day and/or slowly increases the time between breast feedings. Under these conditions, the mother's milk naturally diminishes at a slow rate as the infant's demand lessens.

There are circumstances, however, which either prevent a mother from breastfeeding or require that breastfeeding be discontinued abruptly. Some mothers prefer to bottle-feed rather than breastfeed. The death of an infant results in a mother's sudden halt to breastfeeding. Breastfeeding mothers who become pregnant may be advised to discontinue nursing, especially if the risk for miscarriage is high. Abrupt weaning is recommended for the infant with galactosemia; the infant whose mother uses illegal drugs (American Academy of Pediatrics, Committee on Drugs, 1994); the infant whose mother has untreated active tuberculosis, and the infant whose mother has been infected with the human immunodeficiency virus (American Academy of Pediatrics, Committee on Pediatric Aids, 1995). Whether a mother chooses not to breastfeed at all or to discontinue breastfeeding, lactation will continue for a time. For women who are producing breast milk but not nursing, the milk stasis is associated with swelling of the breast to an extent that may cause conspicuous agony, both physically and psychology.

The cessation of milking or nursing is also associated with increased risk of developing mastitis, a disease caused by intramammary infection (IMI) with pathogens, mostly bacteria, but also yeast, fungi, or even algae. Mastitis can be clinical, with local (and in some cases general) clinical signs and milk abnormalities, or subclinical with production losses and lowered milk quality.

It has been shown that injection of crude preparation of casein hydrolyzate (CNH) comprising proteose-peptones (PPs, also known as casein phosphopeptides, CPP) into the udder of a goat or a cow mimics the natural phenomenon of involution, inducing a local inflammatory response and loss of tight junction (TJ) integrity, followed by rapid drying-off of mammary secretion (U.S. Pat. No. 6,391,849; Shamay et al., 2002 Life Sci. 70:2707-2719; Shamay et al., 2003. J. Dairy Sci. 86:1250-1258). The process induced by CNH was more rapid than that induced at natural drying-off. It was further shown that a pure β-casein (β-CN) fraction 1-28 down-regulates milk secretion in cows and goats. The activity of this peptide was correlated with its ability to block potassium channels in the apical membranes of mammary epithelia (Silanikove et al., 2000. Life Sci. 67:2201-2212).

European Patent Application No. EP1375513 discloses that among the peptides derived from casein, peptides having amino acid sequences comprising plural phosphoserine residues show a strong immuno-enhancing activity. Specifically, the invention relates to an immuno-enhancing agent comprising a peptide consisting of the amino acid sequence Q1-SerP-X-SerP-Q2, wherein, SerP represents the phosphoserine residue, X represents one to three of any amino acid residues, and Q1 and Q2 are independently absent or represents at least one of any amino acid residue.

The inventors of the present invention and co-workers have previously disclosed pharmaceutical compositions comprising casein-derived peptides in the form of a ready to use, sterile, clear solution, substantially devoid of micelles and having a pH above 6.0 (International Patent Application Publication No. WO2006/117784). It was suggested that the minimal active peptide comprises the sequence Ser(p)-Ser(p)-Ser(p)-Glu-Glu. However, these pharmaceutical compositions comprise a plurality of peptides obtained by hydrolysis of casein.

Thus, there is a recognized need for, and would be highly advantageous to have pharmaceutical composition comprising peptides which are defined by their amino acid sequence and concentration. Such composition can be produced on a commercial scale in a reproducible manner.

SUMMARY OF THE INVENTION

The present invention relates to compositions and methods for inducing cessation and attenuation of milk production and involution in a mammary gland of a lactating animal. Particularly, the present invention provides well-defined peptides effective in inducing involution and treating mastitis, pharmaceutical compositions comprising same and use thereof.

The present invention is based in part on the unexpected discovery that a peptide comprising the motif Ser(P)-Ser(P)-Ser(P) linked to at least one positively charged amino acid residue suffice to induce cessation of milk production and involution in a mammary gland of a lactating animal. The contribution of the present invention over the prior art is in providing novel synthetic or recombinant short peptides, that are at least as effective in inducing involution compared to hitherto known compositions for induction of involution comprising casein hydrolyzate. These peptides can be produced easily and reproducibly, essentially with no residues and with high sterility and can be formulated according to the needs.

Thus, according to one aspect, the present invention provides synthetic or recombinant peptide comprising a sequence of 4-7 amino acids of the formula $X_{1(n)}$-Ser(P)-Ser(P)-Ser(P)-$X_{2(n)}$ (SEQ ID NO:1), wherein at least one of $X_1$ and $X_2$ is a positively charged amino acid and wherein at each occurrence n=0, 1 or 2.

According to certain embodiments, the positively charged amino acid is selected from the group consisting of lysine, arginine and histidine. According to certain currently typical embodiments, the positively charged amino acid is lysine.

According to certain typical embodiments, the formula of SEQ ID NO:1 further comprises a blocking group at the C-terminus. According to certain embodiments, the blocking group is selected from the group consisting of amid and ester. Each possibility represents a separate embodiment of the present invention.

According to certain embodiments, the peptide comprises an amino acid sequence selected from the group consisting of:

Lys-Lys-Ser(P)-Ser(P)-Ser(P) (SEQ ID NO:2); Lys-Lys-Ser(P)-Ser(P)-Ser(P)-Lys (SEQ ID NO:3); Lys-Lys-Ser(P)-Ser(P)-Ser(P)-Lys-Lys (SEQ ID NO:4); Lys-Ser(P)-Ser(P)-Ser(P)-Lys-Lys (SEQ ID NO:5); Lys-Ser(P)-Ser(P)-Ser(P)-Lys (SEQ ID NO:6); Lys-Ser(P)-Ser(P)-Ser(P) (SEQ ID NO:7); Ser(P)-Ser(P)-Ser(P)-Lys-Lys (SEQ ID NO:8); and Ser(P)-Ser(P)-Ser(P)-Lys (SEQ ID NO:9). Each possibility represents a separate embodiment of the invention.

According to certain typical embodiments, the peptide comprises the amino acids sequence set forth in SEQ ID NO:2. According to other typical embodiments, the peptide comprises the sequence set forth in SEQ ID NO:2 with amid group at the C-terminus, said sequence is set forth in SEQ ID NO:12.

According to certain embodiments, the peptide has a length of from 4-40 amino acids, typically from 4-30, more typically 4-15 or 4-10 amino acids. According to certain typical embodiments, the peptide consists of SEQ ID NO:2. According to certain other typical embodiments, the peptide consist of SEQ ID NO:12

According to another aspect, the present invention provides a pharmaceutical composition comprising a therapeutically effective amount of a synthetic or recombinant peptide comprising a sequence of 4-7 amino acids of the formula $X_{1(n)}$-Ser(P)-Ser(P)-Ser(P)-$X_{2(n)}$ (SEQ ID NO:1), wherein at least one of $X_1$ and $X_2$ is a positively charged amino acid and wherein at each occurrence n=0, 1 or 2, and a pharmaceutically acceptable diluent or carrier.

According to certain embodiments, the positively charged amino acid is selected from the group consisting of lysine, arginine and histidine. According to certain currently typical embodiments, the positively charged amino acid is lysine.

According to certain typical embodiments, the peptide further comprises a blocking group at the C-terminus. According to certain embodiments, the blocking group is selected from the group consisting of amid and ester. Each possibility represents a separate embodiment of the present invention.

According to certain embodiments, the pharmaceutical composition comprises a peptide comprising the amino acid sequence set forth in any one of SEQ ID NOs 2-9 or a combination thereof. According to certain typical embodiments, the pharmaceutical composition comprises a synthetic or recombinant peptide comprising the amino acid sequence of SEQ ID NO:2, SEQ ID NO:12 or a combination thereof. According to other embodiments, the pharmaceutical composition comprises a peptide consisting of SEQ ID NO:2, SEQ ID NO:12 or a combination thereof.

The pharmaceutical compositions of the present invention can be formulated according to the specific needs, particularly according to the type of the treated population. According to certain embodiments, the pharmaceutical composition is formulated for topical application to a breast or udder as a gel, ointment, cream, emulsion or sustained release formulation including a transdermal patch.

According to other embodiments, the pharmaceutical composition is formulated for parenteral administration. According to certain embodiments the pharmaceutical composition is formulated for intracanal administration, for example by infusion or by injection. When the treated population is a livestock animal, the pharmaceutical composition is formulated for injection into a gland cistern through a teat canal of the mammary gland of the lactating animal. Alternatively, the pharmaceutical compositions of the present invention are formulated for systemic oral administration.

According to additional aspect the present invention provides a method of inducing a transient cessation of milk production, a persistent cessation of milk production or involution in a mammary gland of a lactating mammal, comprising administering to a lactating mammal in need thereof a pharmaceutical composition comprising an effective amount of synthetic or recombinant peptide comprising a sequence of 4-7 amino acids of the formula $X_{1(n)}$-Ser(P)-Ser(P)-Ser(P)-$X_{2(n)}$ (SEQ ID NO:1), wherein at least one of $X_1$ and $X_2$ is a positively charged amino acid and wherein at each occurrence n=0, 1 or 2.

According to certain embodiments, the positively charged amino acid is selected from the group consisting of lysine, arginine and histidine. According to certain currently typical embodiments, the positively charged amino acid is lysine.

According to certain typical embodiments, the peptide further comprises a blocking group at the C-terminus.

According to certain embodiments, the blocking group is selected from the group consisting of amid and ester. Each possibility represents a separate embodiment of the present invention.

According to certain embodiments, the pharmaceutical composition comprises an effective amount of a peptide comprising the amino acid sequence set forth in any one of SEQ ID NOs 2-9 or a combination thereof. According to certain typical embodiments, the peptide comprises SEQ ID NO:2. According to other embodiments, said peptide consists of SEQ ID NO:2.

According to certain embodiments, the lactating mammal is a livestock animal. According to other embodiment, the lactating mammal is a human.

According to certain embodiments, the pharmaceutical composition is administered while the mammary gland is lactating. According to other embodiments, the pharmaceutical composition is administered at the same time milking or nursing is ceasing. In the embodiments wherein the lactating mammal is a livestock animal, the time of cessation of milking includes, but is not limited to, the time in which a dry off period is induced previous to calving. Single administration as well as multiple administrations is contemplated.

Typically, the pharmaceutical composition is administered once or several times, typically 1 to 6 times, more typically 1 to 3 times, at an interval selected from the group consisting of about 2 hours, about 6 hours, about 8 hours, about 12 hours, about 16 hours, about 20 hours, about 24 hours, about 48 hours or about 72 hours. According to one currently typical embodiment, the pharmaceutical composition is administered only once.

According to additional embodiments, wherein the lactating mammal is a livestock animal, cessation of milking occurs about 60 to 70 days before an expected parturition, typically about 40 to 60 days, or between about 20 to about 40 days before an expected parturition. Accordingly, the pharmaceutical composition is administered about 60 to 90 days before an expected parturition, typically about 40 to 60 days, or between about 20 to about 40 days before an expected parturition.

According to certain embodiments cessation of milk production is observed within around 2-3 days after peptide administration, without negatively affecting re-constitution of the mammary gland tissues towards the next lactating period. The peptides of the present invention can be administered at any stage of the lactation cycle, including at the peak of lactation.

As described hereinabove, abrupt cessation of milking and the induction of involution lead to a higher risk and a higher incidence of intramammary infections and mastitis. The rapid induction of involution by the peptides and compositions of the invention significantly reduces the incidences of mastitis caused by cessation of milking. Furthermore, the peptides of the present invention are efficient in treating and alleviating mastitis. Thus, according to certain aspects, the present invention provides a method for preventing, treating and reversing a microbiological infection, comprising administering to a lactating animal the pharmaceutical compositions of the present invention.

According to certain embodiments, the method comprises topical or parenteral administration of the pharmaceutical composition. According to some embodiment, the method comprises intracanal administration of the pharmaceutical composition comprising the peptide(s). According to certain typical embodiments, the pharmaceutical composition is administered into a teat canal of a mammary gland of the lactating mammal. Administration to the teat canal can be by way of injection or infusion. According to other typical embodiments, the composition is administered topically to the mammary gland. The composition can be administered to one or more mammary glands, including concomitant administration to all mammary glands of the lactating mammal. The composition may be administered at any stage of lactation.

According to additional embodiments, the method further comprises co-administering an anti-microbial therapy selected from the group consisting of an antibiotic and a bactericide; an immunomodulator; an anti-inflammatory therapy or a combination thereof. In one embodiment, the method further comprises the administration of a non-antibiotic teat seal or a teat seal in combination with an antibiotic, a bactericide or an immunomodulator. According to certain embodiments, the therapy is selected from the group consisting of antibiotic, bactericide, steroidal and non-steroidal anti-inflammatory treatment, treatment with an immunomodulator and vaccination. Administering the anti-microbial therapy is useful, in certain embodiments, for preventing a potential infection resulting from the process of administering a pharmaceutical composition into a teat canal of a mammary gland, particularly when administration is performed at a herd site.

It is to be understood explicitly that the scope of the present invention encompasses one or more amino acid substitution, as well as amino acid derivatives, non-natural amino acids and synthetic acids as are known in the art, with the stipulation that these variants and modifications must preserve the capacity of inducing involution in a mammary gland of the original molecule in the context of the present invention.

Other objects, features and advantages of the present invention will become clear from the following description and drawings.

DETAILED DESCRIPTION OF THE INVENTION

The present invention provides novel synthetic or recombinant peptides that are highly efficient in inducing a process of involution and cessation of milk production in a mammary gland of a lactating mammal, including a lactating livestock animal and a lactating human.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Definitions

The term "peptide" is used throughout the specification to designate a linear series of amino acid residues connected one to the other by peptide bonds. The peptides according to the principles of the present invention are synthetic or recombinant and are other than any known intact protein.

As used herein, the term "phosphopeptide" designates a phosphorylated peptide in form of a conjugated peptide in which the non-peptide portion is a residue of phosphoric acid. In particular the expression "phosphopeptide" or "phosphoserine" designates conjugated serine in which the non-peptide portion is a residue of phosphoric acid.

As used herein, the term "cessation of milk production" refers to transient cessation as well as to persistent cessation of milk production. Transient cessation of milk production refers to reversible cessation. Persistent cessation refers to interruption in lactation which is reversible only by parturition following pregnancy and/or by sexual hormonal treatment. According to the teaching of the present invention, mechanical stimuli (i.e., milking or nursing) can reverse a transient cessation of milk production induced by the compositions and methods of the invention.

The term "involution" as used herein refers to the complex process of controlled apoptosis and tissue remodeling within the mammary gland, which results in cessation of milk production by the mammary gland. During the initial stages of involution, apoptotic death of endothelial cells typically results in an increase in the somatic cell count within the residual milk secretions.

As used herein the term "mastitis" refers to an inflammation of a mammary gland, a breast or an udder, caused by a physical injury, introduction of chemicals, viruses, fungus, parasites or, most commonly, bacterial invasion and their toxins. "Mastitis" is used to describe all forms of such inflammation, including subclinical and clinical mastitis, clinical mastitis including mild, severe and chronic mastitis.

In sub-clinical mastitis, no swelling of the breast or udder is detected nor are there observable abnormalities in the milk. This type of mastitis is commonly referred to as "subclinical". In livestock animals, especially dairy cows, special screening tests, including the California Mastitis Test (CMT), Wisconsin Mastitis Test (WMT) based on an estimation of somatic cell counts and the catalase test will show changes in the milk composition in case of subclinical mastitis. Clinical mastitis can be mild or acute, and is characterized by the presence of leukocytes in the milk. Mild clinical mastitis involves changes in the milk appearance including presence of flakes or clots, watery milk or other unusual forms of the milk. Mild clinical mastitis may be accompanied by other symptoms including hot, sensitive or swollen breast or udder.

Severe clinical mastitis involves the symptoms of hot, sensitive, firm breast or udder that is quite painful to the lactating subject. The onset of severe clinical mastitis is sudden and the lactating subject may become ill showing signs of fever, rapid pulse, depression, weakness and loss of appetite. When the whole lactation system of the subject is affected, the condition is referred to as acute systemic mastitis. The severe symptoms may be also accompanied with cessation of milk production.

Chronic mastitis is persistent udder or breast infection, typically in the form of subclinical mastitis, which occasionally can develop into the clinical form and back to the subclinical form. Chronic mastitis is characterized by hard lump within the mammary gland due to the establishment of bacteria and the formation of excessive connective tissue.

Preferred Modes of Practicing the Invention

According to one aspect, the present invention provides synthetic or recombinant peptide comprising a sequence of 4-7 amino acids of the formula $X_{1(n)}$-Ser(P)-Ser(P)-Ser(P)-$X_{2(n)}$ (SEQ ID NO:1), wherein at least one of $X_1$ and $X_2$ is a positively charged amino acid and wherein at each occurrence n=0, 1 or 2.

According to certain embodiments, the positively charged amino acid is selected from the group consisting of lysine, arginine and histidine. According to certain currently typical embodiments, the positively charged amino acid is lysine.

The peptides of the present invention can be synthesized using methods well known in the art including chemical synthesis and recombinant DNA technology. Synthesis can be performed in solution or by solid phase peptide synthesis as described by Merrifield (see J. Am. Chem. Soc., 85:2149, 1964). Typically, the peptides are synthesized by using standard solid phase techniques. These methods include exclusive solid phase synthesis, partial solid phase synthesis methods, fragment condensation and classical solution synthesis. Solid phase peptide synthesis procedures are well known in the art and are further described by e.g. John Morrow Stewart and Janis Dillaha Young, Solid Phase Peptide Syntheses (2nd Ed., Pierce Chemical Company, 1984).

Phosphorylation of the Serine residues can be performed by any method as is known in the art, as described for example in Meggio et al., 1991. FEBS Lett. 283(2):303-306 and Perich J W 1997. Method Enzymol. 289:245-246, among others.

In general, peptide synthesis methods comprise the sequential addition of one or more amino acids or suitably protected or derivatized amino acids to a growing peptide chain. Normally, either the amino or the carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) may be removed sequentially or concurrently, to afford the final peptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

Synthetic peptides can be purified by preparative high performance liquid chromatography (Creighton T. 1983. Proteins, structures and molecular principles. WH Freeman and Co. N.Y.) and the composition of which can be confirmed via amino acid sequencing.

The peptides of the present invention can also be generated using recombinant techniques as are known in the art, such as described, for example, by Bitter et al., (1987) Methods in Enzymol. 153:516-544 and Studier et al. (1990) Methods in Enzymol. 185:60-89.

According to certain typical embodiments, the carboxyl group at the C terminus of the peptide is protected. The protecting group is selected from, but not limited to an amide (i.e., the hydroxyl group at the C terminus is replaced with $NH_2$, $NHR_2$ and $NR_2R_3$) or ester (i.e. the hydroxyl group at the C terminus is replaced with $OR_2$). $R_2$ and $R_3$ are optionally independently an aliphatic, substituted aliphatic, benzyl, substituted benzyl, aryl or a substituted aryl group. In addition, taken together with the nitrogen atom, $R_2$ and $R_3$ can optionally form a $C_4$ to $C_8$ heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C terminal protecting groups include but are not limited to —$NH_2$, —$NHCH_3$, —$N(CH_3)_2$, —NH(ethyl), —N(ethyl)$_2$, —N(methyl) (ethyl), —NH(benzyl), —N($C_1$-$C_4$ alkyl)(benzyl), —NH(phenyl), —N(C$_1$-C$_4$ alkyl) (phenyl), —OCH$_3$, —O-(ethyl), —O-(n propyl), —O-(n butyl), —O-(iso-propyl), —O-(sec butyl), —O-(t butyl), —O-benzyl and —O-phenyl.

According to certain currently typical embodiments, the C terminus of the peptide is protected by amid.

According to certain embodiments, the peptide comprises an amino acid sequence selected from the group consisting of Lys-Lys-Ser(P)-Ser(P)-Ser(P) (SEQ ID NO:2); -Lys-Lys-Ser(P)-Ser(P)-Ser(P)-Lys (SEQ ID NO:3); Lys-Lys-Ser(P)-Ser(P)-Ser(P)-Lys-Lys (SEQ ID NO:4); Lys-Ser(P)-Ser(P)-Ser(P)-Lys-Lys (SEQ ID NO:5); Lys-Ser(P)-Ser(P)-Ser(P)-Lys (SEQ ID NO:6); Lys-Ser(P)-Ser(P)-Ser(P) (SEQ ID NO:7); Ser(P)-Ser(P)-Ser(P)-Lys-Lys (SEQ ID NO:8); and Ser(P)-Ser(P)-Ser(P)-Lys (SEQ ID NO:9). Each possibility represents a separate embodiment of the invention.

According to certain typical embodiments, the peptide comprises the amino acids sequence set forth in SEQ ID NO:2.

According to certain embodiments, the peptide has a length of from 4-40 amino acids, typically from 4-30, more typically 4-15 or 4-10 amino acids. According to certain typical embodiments, the peptide consists of SEQ ID NO:2.

According to another aspect, the present invention provides a pharmaceutical composition comprising a therapeutically effective amount of a peptide of the invention.

Hitherto known compounds and composition for inducing involution and cessation of milking in a lactating mammal were typically obtained by hydrolysis of casein and/or purification of the relevant peptides from the hydrolyzate. Having small and defined peptides that are effective in inducing cessation of milk production and involution is highly desired as such peptides may be synthesized consistently. Furthermore, the process of peptide synthesis is less prone to contamination compared to processes involving peptide purification from natural source material. The peptides of the invention are at least as efficient, typically more efficient compared to the known casein-derived peptides.

The term "pharmaceutical composition" is intended in its broad sense and refers to a preparation of one or more of the peptides of the invention with other chemical components such as pharmaceutically suitable diluents and carriers. The purpose of a pharmaceutical composition is to facilitate administration of a compound to an organism. The pharmaceutical composition of the invention should contain a therapeutic amount of a peptide of the invention, i.e., that amount necessary for inducing cessation of milk production and involution.

According to certain embodiments, the peptide concentration in the pharmaceutical composition is from about 1 μg/ml to about 5000 μg/ml, typically between 40 μg/ml to about 800 μg/ml.

The term "pharmaceutically acceptable carrier" as used herein, refers to a carrier or a diluent that does not cause significant irritation to an organism and does not abrogate the biological activity and properties of the administered compound. Non-limiting examples of carriers are: water, propylene glycol, saline, emulsions and mixtures of organic solvents with water. Techniques for formulation and administration of drugs may be found in "Remington's Pharmaceutical Sciences," Mack Publishing Co., Easton, Pa., latest edition, the contents of which are incorporated herein by reference. According to certain embodiments, the pharmaceutical compositions of the present invention are formulated for parenteral administration, e.g. for intracanal administration, particularly for injection or infusion into the teat canal of a mammary gland. For injection, the peptides of the invention can be formulated in aqueous solutions, preferably in physiologically compatible buffers such as Hank's solution, Ringer's solution, or in physiological saline buffer with or without organic solvents such as propylene glycol and polyethylene glycol. Intracanal administration to a teat canal of a mammary gland is not defined in terms of topical or systemic administration. As disclosed herein, intracanal administration of the pharmaceutical composition of the invention can have a local effect, for example by inducing involution only in the treated mammary gland, and may therefore be referred to as topical. The pharmaceutical compositions may be also administered topically as a gel, ointment, cream, emulsion or sustained release formulation including a transdermal patch. The present invention further encompasses systemic administration, either parenterally or orally.

According to additional aspect the present invention provides a method of inducing a transient cessation of milk production, a persistent cessation of milk production or involution in a mammary gland of a lactating mammal, comprising administering to a lactating mammal in need thereof a pharmaceutical composition comprising an effective amount of synthetic or recombinant peptide comprising a sequence of 4-7 amino acids of the formula $X_{1(n)}$-Ser(P)-Ser(P)-Ser(P)-$X_{2(n)}$ (SEQ ID NO:1), wherein at least one of $X_1$ and $X_2$ is a positively charged amino acid and wherein at each occurrence n=0, 1 or 2.

According to a further aspect the present invention provides a pharmaceutical composition comprising an effective amount of synthetic or recombinant peptide comprising a sequence of 4-7 amino acids of the formula $X_{1(n)}$-Ser(P)-Ser(P)-Ser(P)-$X_{2(n)}$ (SEQ ID NO:1), wherein at least one of $X_1$ and $X_2$ is a positively charged amino acid and wherein at each occurrence n=0, 1 or 2 for inducing a transient cessation of milk production, a persistent cessation of milk production or involution in a mammary gland of a lactating mammal.

According to certain embodiments, the positively charged amino acid is selected from the group consisting of lysine, arginine and histidine. According to certain currently typical embodiments, the positively charged amino acid is lysine.

According to certain typical embodiments, the peptide further comprises a blocking group at the C-terminus. According to certain embodiments, the blocking group is selected from the group consisting of amid and ester. Each possibility represents a separate embodiment of the present invention.

According to certain embodiments, the lactating mammal is selected from the group consisting of humans, cows, goats, sheep, buffalos, camels, donkeys, llamas, horses, pigs, cats and dogs.

According to certain currently typical embodiments, the lactating animal is a human. In humans, production of milk without nursing may be a result of the woman own decision not to breastfeed or of a condition preventing the breast feeding as described herein above. Such milk stasis is associated with swelling of the breast to an extent that causes pain, is frequently associates with leaking of the mammary secretion that subsequently increases the risk of acquiring intramammary infection. The pharmaceutical compositions and methods of the present invention thus answer the need for a rapid and efficient induction of involution and cessation of milk production as to prevent the above-described undesirable conditions.

According to additional currently typical embodiments, the animal is a livestock animal selected from the group consisting of cows, buffalos, goats, sheep and pigs. According to certain currently typical embodiments, the livestock animal is dairy cow.

In the modern dairy industry, the lactating animal gives birth once a year, such that milking continues while the animal is pregnant. Imposing the dry period on a lactating animal before parturition is a practice taken to induce the process of involution in the mammary gland, so as to enable the restoration of the mammary tissue towards the next lactating period. Inducing the dry period is necessary, inter alia, to maintain similar milk yield before and after parturition. In cows, the natural process of involution is completed about 21 to 30 days after its induction by cessation of milking. The present invention now discloses that surprisingly, the synthetic or recombinant peptides of the invention induce cessation of milk production and the process of involution.

The transient or persistent effect on milk production can be obtained in a mammary gland of a lactating animal in response to application of the pharmaceutical composition of the invention, typically by direct injection or infusion into the gland cistern through the teat canal. Cessation of milk production can occur only in the treated gland or in all mammary glands treated. Administration can be performed at any stage of the lactation period. In the embodiments wherein the lactating mammal is a livestock animal, administration can be also performed during the so-called dry-off period.

The involution process induced by the synthetic or recombinant peptides and pharmaceutical compositions of the present invention may be more rapid and synchronized compared to involution induced by cessation of milking, and milk production can be resumed by mechanical stimuli like milking. Resumption of milk production may also occur, as in the natural process of involution, after a subsequent pregnancy and parturition. The involution induced by the compositions of the present invention does not interfere with re-building of the mammary gland tissue and restoration of milk secretion capacity towards parturition.

The involution induced by the peptides and compositions of the invention prevents intramammary infection and mastitis typically associated with abrupt cessation of milking. Thus, the compositions of the invention are useful for preventing of an infection of the mammary gland. Additionally, the peptides and compositions of the invention are useful in treating and curing intramammary infection, including infections related to permanent or transient cessation of milking.

According to additional embodiments, the peptides and compositions of the present can be used to promote skin regeneration capabilities around the mammal teat.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

All experiments are performed in accordance with the guidelines for Regulation of Animal Experiments in the State of Israel, and according to the Ethics Committee of the Research Institution.

Example 1

Peptide Synthesis

The synthetic peptides of the invention were designed as to assess the activity of short peptides comprising a Ser(P) motif on involution. Peptides having the same sequence but with non-phosphorylated serine residues were also synthesized to examine the function of phosphorylation on the peptide activity. Casein-derived peptide as well as casein hydrolyzate served as positive controls.

Ten peptides were chemically synthesized employing the solid phase of fluorenylmethyloxycarbonyl (Fields G. B. & Nobel R. 1990. Int. J. Peptide Protein Res. 35:161-214). The C-terminal α-carboxyl group of each peptide was converted to an amide group. For each peptide including the phosphoserine motif, a control peptide having the same sequence but with un-phosphorylated serine was synthesized. Table 1 below shows the sequences of all the synthesized peptides.

TABLE 1

Sequences and codes for the synthetic peptides

| Assay and Formulation Code | Analysis Code | Sequence | SEQ ID NO. |
|---|---|---|---|
| P241210-01-01 | A(p) | Lys-Lys-Ser(P)-Leu-Ser(P)-Ser(P)-Ser(P)-NH$_2$ | 10 |
| P241210-01-02 | A | Lys-Lys-Ser-Leu-Ser-Ser-NH$_2$ | 11 |
| P241210-01-03 | B(p) | Lys-Lys-Ser(P)-Ser(P)-Ser(P)-NH$_2$ | 12 |
| P241210-01-04 | B | Lys-Lys-Ser-Ser-Ser-NH$_2$ | 13 |
| P241210-01-05 | C(p) | Lys-Lys-Ser(P)-Ser(P)-NH$_2$ | 14 |
| P241210-01-06 | C | Lys-Lys-Ser-Ser-NH$_2$ | 15 |
| P241210-01-07 | D(p) | Glu-Ser(P)-Leu-Ser(P)-Ser(P)-Ser(P)-Glu-Glu-NH$_2$ | 16 |
| P241210-01-08 | D | Glu-Ser-Leu-Ser-Ser-Ser-Glu-Glu-NH$_2$ | 17 |
| P241210-01-09 | E(p) | Lys-Ser(P)-Ser(P)-Ser(P)-Glu-Glu-NH$_2$ | 18 |
| P241210-01-010 | E | Lys-Ser-Ser-Ser-Glu-Glu-NH$_2$ | 19 |

All peptides were validated by time-of-flight mass spectrometry. Purity was measured by reverse-phase high performance liquid chromatography method and was found to be at least 98%. All dried chemically synthesized fragments are stored at −20° C.

Example 2

Preparation of Casein Hydrolyzate

Casein hydrolyzate is known to be effective in inducing involution in a mammary gland (e.g. U.S. Pat. No. 6,391,849; Shamay et al., 2002 ibid; Shamay et al., 2003 ibid). Thus, casein hydrolyzate was prepared as a positive control in assessing the peptides activity of inducing involution.

Sodium caseinate (DMV Int., NL) at a total weight of 4000 gr was added into a 25 mM Tris HCl solution pH=8.0 to produce a 20% (w/v) solution. After the sodium caseinate was added the solution was gently stirred to equilibration, while keeping the pH at 8.0 and the temperature at 45° C. The sodium caseinate typically dissolves in approximately 15-60 minutes to produce a final 20% (w/v) solution.

Four (4) gr porcine trypsin powder was then added at 1:1000 trypsin:sodium caseinate ratio, and the solution was stirred gently on magnetic or deflocculating stirrer under gentle agitation at 45° C. The hydrolysis was allowed to proceed for a total of 1 hour.

At the end of the time set for hydrolysis, trypsin was inactivated within the crude hydrolyzate by elevating the temperature to 90-95° C. and holding the solution at this temperature range for 1 hour. After 1 hour the solution was cooled to room-temperature by using ice in an external bath and the pH was adjusted to 4.7 using 10N HCl. The solution was kept in this pH for 15-30 minutes.

Insoluble material was removed from the solution by centrifugation for 20 min, at 2-8° C., 4500 rpm (~4400 g) using IEC centrifuge (model DPR 6000, Damon\IEC division). The resulted supernatant was transferred to a new sterile glass bottle, and the pH was adjusted to 7.0 using 10N NaOH. The solution volume was then adjusted to 20 liter with 25 mM Tris HCl solution, pH 7.0.

The final supernatant obtained was filtered through 3.0 μm/1.2 μm/0.65 μm pre-filters and through two 0.45/0.22 μm sterile CA membrane filter capsules [Sartopure PP2 3.0 μm filter capsule (Sartorius, Cat. No. 5592502P1), Sartoclean DGF 1.2 μm filter capsule (Sartorius, Cat. No. 5642803A1), Sartoclean GF 0.8/0.65 μm filter capsule (Sartorius, Cat. No. 5602805G1)]

Glass serum bottle (20 ml, 50 ml, 100 ml and 200 ml) were filled with 20 ml, 40 ml, 90 ml or 170 ml respectively of the filtrated solution by aseptic filling in sterile bench (class 100, ISO 5) located in a clean room class 1000 (ISO 6). Each bottle was sealed with aluminum seal using crimpers. The resulted casein hydrolyzate was kept frozen at 20° C. until use.

Example 3

Formulation of the Synthesized Peptides

Each of the chemically synthesized peptides was dissolved in saline up to 7 days prior to administration. Stability tests of up to 7 days showed a stability of above 98% for these products. The peptide concentration was 0.4 mg/ml saline. 10 ml samples were kept in vials at 4° C.-8° C. until use. Administration dose was 4 mg (10 ml solution).

Example 4

A Field Study Examining the Induction of Involution by the Isolated Peptides

Changes in the composition of mammary secretions during early involution reflect increased transfer of blood-derived factors and decreased synthesis and secretion of lacteal fluid. For example, the concentration of lactose decreases markedly during the days of involution, while the concentrations of the plasmin-plasminogen activator and the pH of the mammary secretions increase during the early non-lactating period (Oliver and Sordillo 1989. J Dairy Sci. 1989; 72:1647-1664).

A filed study was performed to assess the potential of a single intramammary dose of the synthetic peptides of the invention administered at dry (i.e. at the day in which milking is ceased), to induce rapid involution.

Study Design

Total of 107 dairy cows were enrolled to the study, of which 45 received treatment and 62 served as a control. All cows were dairy cows at their first or further lactation that stand the inclusion/exclusion criteria. The study was a controlled blinded case-control study.

Case subjects received one dose by intramammary infusion of a particular peptide. Controls were lactating cows that received the following products by intramammary administration:
i) De-phosphorylated peptides;
ii) Casein hydrolyzate.

Treatment Groups

Case Groups

Five groups of 9 cows (total of 36 udder quarters per group) were scheduled as case groups. Each group was treated with one out of the five (5) phosphopeptides described in Example 1 hereinabove (P241210-01-01; 03; 05; 07 and 09). The peptides were administered once via intramammary infusion of 10 ml containing 4 mg peptide.

Control Groups

Set one: Five groups of 9 cows (total of 36 udder quarters per group) were scheduled as a first control set. Each group was treated with one out of the five (5) dephosphorylated peptides described in Example 1 hereinabove (P241210-01-02; 04; 06; 08 and 10). The peptides were administered once via intramammary infusion of 10 ml containing 4 mg peptide.

The second control set included:
(i) Eleven cows (total of 44 udder quarters) treated with casein hydrolyzate (20 ml) administered once via intramammary infusion of 20 ml (around 1.8 mg/ml casein phosphopeptide (CPP), total=36 mg CPP for 20 ml)
ii) Six cows (24 udder quarters) that received saline solution (10 ml) via intramammary infusion.

The cows enrolled to the study were selected from three herds. The case cows, receiving each of the peptides identified by a batch number ending with a non-pair number (i.e., MLT-P241210-01-01, MLT-P241210-01-03, MLT-P241210-01-05, MLT-P241210-01-07, and MLT-P241210-01-09), were selected from the herds participating in the study. Subsequently, the cows that received peptides having consecutive batch number (pair ended, i.e., MLT-P241210-01-02, MLT-P241210-01-04, MLT-P241210-01-06, MLT-P241210-01-08, and MLT-P241210-01-10) were allocated from the same herds.

Control subject treated with casein hydrolyzate or saline solution were distributed and matched to the case subjects. Distribution of the last control group was distributed in a proportion to each of the herds included in the study.

Exclusion Criteria

Cows falling under one or more of the definitions below were not enrolled into the study:
Cows that received antibiotic therapy for mastitis or for any other condition in a period of 4 weeks prior to dry-off;
Cows having less than four (4) fully-functional quarters;
Non-lactating cows;
Cows with evidence of clinical mastitis (such as pain, redness, swelling or warmth in the mammary gland, abnormal milk secretion, depression, reduced feed intake, general discomfort, or other indications);
Cows showing other health conditions identified by the Investigator that preclude enrollment;
Cows intended for culling.

Treatment

All treatments (peptides, casein hydrolyzate and saline) were administered at the time point scheduled for cessation of milking (dry off). The day of administration was set as Day 0.

Sampling and Measurements

Sets of aseptic milk samples were collected in two separate vials once a day in the milking facility after the morning milking, on Day 0 and in post-treatment days 1, 2 and 3. The sampling time points were set to up to three days after treatment administration to ensure sufficient milk secretion for the measurements of all involution parameters. The volume of the samples was between 30 to 50 ml. The pH of the milk sample was measured in situ using a Cyberscan pH11 meter (Eutech Instruments, Singapore). The apparatus was calibrated each day by immersing the receptor in standard buffers of pH 7.0 and pH 4.01. Measurements were taken twice for each sample obtained from a mammary gland, with an interval of 30 seconds between measurements. pH measurement was repeated on-site by using the same sample vial. Before double-pH measurement, the milk sample vials were gently shaken three (3) times. After the pH measurement, the milk samples vials were kept in cool storage with a preservative product (Broad Spectrum Microtabs II—Bronopol and Metamycin—D&F Control System Inc., Two Technology Way, Norwood Mass. 02062 USA).

Lactose values in the milk samples were determined at the Central Laboratory of Milk Quality, Caesaria Industrial Park, Israel, according to ISO 2266211DF 198:2007.

Somatic cell count was also determined in milk samples by Fossomatic 360 (Foss Electric, Hillerod, Denmark), and based on guidelines from the USA National Mastitis Council. Laboratory Handbook on Bovine Mastitis. 1999. Ed. National Mastitis Council, Verona, Wis. 53593 USA.

Standard dry cow management practice was applied at each site after treatment application, with clinical observations of cows enrolled into the study during the subsequent three days. The clinical observation included administration of medications (type of drugs, doses, routes of administration), physical examination (at investigator decision) and monitoring of adverse events. After three days the cows were managed according to the regular herd schedule.

Data from six quarters were excluded from the analysis of lactose changes. Data from one of those quarters were omitted due to a missing initial value. For the other five quarters, lactose concentrations taken during the three follow-up days could not be analyzed due to a rapid mammary involution process, resulting in non-sufficient milk sample for lactose analysis.

Sample Size

The primary pivotal variable was set as the classification of involution success. The calculated minimal sample size for each serine peptide to be tested was 36 quarters (nine cows). Assumptions for the calculation were: a success percentage of 55% for phosphoserine peptides vs. a success percentage of 35% for the dephosphoserine peptides, and a power of 80% to reach a significance of 5%.

RESULTS

Endpoint Measures: pH, lactose and somatic cell counts (SCC) values from milk secretions at day 0 and during three (3) days post-treatment were taken. Results are described as the difference between the measures at each of the 3 days post treatment and the measured level at Day 0. The results are presented in Tables 1-3 hereinbelow.

pH

The pH of the milk produced in a mammary gland after induction of the involution process increases, mainly suggesting rupture of the tight junction of the mammary gland. Table 2 below summarizes the effect of the peptides examined and of casein hydrolyzate (CNH) on the pH of milk samples taken 1, 2 and 3 days after the one-dose treatment with each peptide or CNH. The results are presented as the difference in pH value between each of the days post treatment and Day 0 (before treatment).

TABLE 2

Changes of pH in milk samples across the study

| Treatment | Day 1 | | Day 2 | | Day 3 | |
|---|---|---|---|---|---|---|
| | Mean | SE | Mean | SE | Mean | SE |
| A(p) (SEQ ID NO: 10) | 0.016 | 0.017 | 0.020 | 0.037 | 0.118 | 0.036 |
| A (SEQ ID NO: 11) | 0.048 | 0.018 | −0.002 | 0.021 | 0.072 | 0.021 |
| B(p) (SEQ ID NO: 12) | 0.171 | 0.026 | 0.165 | 0.035 | 0.163 | 0.033 |
| B (SEQ ID NO: 13) | −0.015 | 0.013 | −0.019 | 0.017 | 0.065 | 0.020 |
| C(p) SEQ ID NO: 14) | 0.066 | 0.020 | 0.046 | 0.025 | 0.119 | 0.035 |
| C (SEQ ID NO: 15) | 0.034 | 0.013 | −0.006 | 0.019 | −0.001 | 0.028 |
| D(p) (SEQ ID NO: 16) | 0.027 | 0.015 | −0.018 | 0.019 | 0.077 | 0.025 |
| D (SEQ ID NO: 17) | 0.000 | 0.012 | −0.027 | 0.012 | 0.013 | 0.021 |
| E(p) (SEQ ID NO: 18) | 0.045 | 0.012 | 0.061 | 0.028 | 0.128 | 0.034 |
| E (SEQ ID NO: 19) | 0.047 | 0.018 | −0.028 | 0.052 | 0.115 | 0.032 |
| Casein Hydrolyzate | 0.083 | 0.018 | 0.106 | 0.023 | 0.167 | 0.033 |

As apparent from Table 1, peptide B(p), having SEQ ID NO:12, Lys-Lys-(SerP)-(SerP)-(SerP)-NH$_2$ (i.e. SEQ ID NO:2 with amid as blocking group at the C-terminus) showed the most significant effect on the milk pH, particularly at the first 2 days after treatment. Administration of casein hydrolyzate reached the magnitude of the effect of peptide B(p) only at the third day. It is to be noted that the effect of the novel peptide of the invention was superior of the effect of the casein-derived peptides D(p) (SEQ ID NO:16) and E(p) (SEQ ID NO:18).

Lactose

One of the most significant outcomes of involution in terms of milk composition is a reduction in lactose content. Thus, lactose concentration was also measured in the milk samples taken before and after peptide or CNH administration as described for the pH measurements hereinabove. Table 3 summarizes the changes in lactose concentration between milk samples taken at each time point and a sample taken at Day 0 (before treatment).

TABLE 3

Changes in Lactose content in milk samples across the study

| Treatment | Day 1 | | Day 2 | | Day 3 | |
|---|---|---|---|---|---|---|
| | Mean | SE | Mean | SE | Mean | SE |
| A(p) (SEQ ID NO: 10) | −0.462 | 0.071 | −1.364 | 0.122 | −1.771 | 0.130 |
| A (SEQ ID NO: 11) | −0.463 | 0.060 | −1.268 | 0.109 | −1.773 | 0.160 |
| B(p) (SEQ ID NO: 12) | −1.250 | 0.164 | −2.013 | 0.132 | −2.521 | 0.140 |
| B (SEQ ID NO: 13) | −0.320 | 0.105 | −0.969 | 0.103 | −1.412 | 0.158 |
| C(p) SEQ ID NO: 14) | −0.509 | 0.195 | −1.427 | 0.173 | −0.345 | 0.220 |
| C (SEQ ID NO: 15) | −0.846 | 0.126 | −1.554 | 0.110 | −0.387 | 0.242 |
| D(p) (SEQ ID NO: 16) | −0.431 | 0.083 | −1.460 | 0.088 | −2.180 | 0.103 |

TABLE 3-continued

Changes in Lactose content in milk samples across the study

| Treatment | Day 1 Mean | Day 1 SE | Day 2 Mean | Day 2 SE | Day 3 Mean | Day 3 SE |
|---|---|---|---|---|---|---|
| D (SEQ ID NO: 17) | −0.749 | 0.201 | −1.387 | 0.188 | −0.090 | 0.174 |
| E(p) (SEQ ID NO: 18) | −0.354 | 0.075 | −1.530 | 0.089 | −2.042 | 0.120 |
| E (SEQ ID NO: 19) | −0.368 | 0.077 | −1.531 | 0.141 | −1.675 | 0.202 |
| Casein hydrolyzate | −0.293 | 0.121 | −1.048 | 0.124 | −1.383 | 0.205 |

In all time point examined, peptide B(p) had a higher effect on the reduction of lactose content compared to the effect of CNH, known to be highly effective in inducing involution. Peptide B(p) showed also higher effect compared to the casein-derived peptides D(p) and E(p). However, after three days the effect of the peptide B(p) was similar to the effect of the casein-derived peptide D(p).

Somatic Cell Counts

Additional parameter that may be used to establish the progression of the involution process is the presence of somatic cells within the milk. The increase in cell count within the milk is the result of high degree of apoptotic epithelial cell death associated with involution. Table 4 below shows the changes in somatic cell counts (SCC) as compared to Day 0 (see above). The results presented in the table were calculated from log transformation of the raw data that were highly variable.

TABLE 4

Changes in Somatic Cell Counts in milk samples across the study

| Treatment | Day 1 Mean | Day 1 SE | Day 2 Mean | Day 2 SE | Day 3 Mean | Day 3 SE |
|---|---|---|---|---|---|---|
| A(p) (SEQ ID NO: 10) | 0.592 | 0.176 | 1.212 | 0.195 | 1.829 | 0.236 |
| A (SEQ ID NO: 11) | 0.911 | 0.202 | 1.571 | 0.161 | 2.090 | 0.183 |
| B(p) (SEQ ID NO: 12) | 3.129 | 0.141 | 3.099 | 0.231 | 3.451 | 0.181 |
| B (SEQ ID NO: 13) | 0.109 | 0.191 | 0.664 | 0.182 | 1.191 | 0.216 |
| C(p) SEQ ID NO: 14) | −0.129 | 0.342 | 0.961 | 0.273 | 0.195 | 0.308 |
| C (SEQ ID NO: 15) | 0.511 | 0.204 | 1.194 | 0.211 | 0.650 | 0.326 |
| D(p) (SEQ ID NO: 16) | 0.383 | 0.214 | 1.181 | 0.209 | 1.998 | 0.202 |
| D (SEQ ID NO: 17) | 0.387 | 0.290 | 1.023 | 0.240 | −0.249 | 0.270 |
| E(p) (SEQ ID NO: 18) | 0.060 | 0.158 | 1.175 | 0.176 | 1.847 | 0.226 |
| E (SEQ ID NO: 19) | −0.186 | 0.172 | 0.843 | 0.258 | 1.492 | 0.207 |
| Casein hydrolyzate | 0.181 | 0.182 | 0.818 | 0.179 | 1.048 | 0.256 |

Concomitant with the results obtained for the effect of the tested peptides on the pH value and lactose content in the milk, peptide B(p) was found to be superior to casein hydrolyzate or to casein derived peptides. It is thus concluded that this peptide is highly effective in inducing involution.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A synthetic or recombinant peptide comprising a sequence of 4-7 amino acids of the formula $X_{1(n)}$-Ser(P)-Ser(P)-Ser(P)-$X_{2\ (m)}$-(SEQ ID NO:1), where Ser(P) represents phosphorylated serine, wherein at least one of $X_1$ and $X_2$ is a positively charged amino acid and wherein n+m=1-4, wherein the formula of SEQ ID NO:1 further comprises a blocking group at the C-terminus.

2. The synthetic or recombinant peptide of claim 1, wherein the positively charged amino acid is selected from the group consisting of lysine, arginine and histidine.

3. The synthetic or recombinant peptide of claim 2, wherein the positively charged amino acid is lysine.

4. The synthetic or recombinant peptide of claim 1, wherein the blocking group is selected from amid and ester.

5. The synthetic or recombinant peptide of claim 1, said peptide comprises the amino acid sequence set forth in any one of SEQ ID NOs: 2-9.

6. The synthetic or recombinant peptide of claim 5, said peptide consists of SEQ ID NO:2.

7. The synthetic or recombinant peptide of claim 4, said peptide comprises the amino acid sequence set forth in SEQ ID NO:12.

8. A pharmaceutical composition comprising a pharmaceutically acceptable diluent or carrier and a therapeutically effective amount of a synthetic or recombinant peptide comprising a sequence of 4-7 amino acids of the formula $X_{1(n)}$-Ser(P)-Ser(P)-Ser(P)-$X_{2(m)}$ (SEQ ID NO:1), where Ser(P) represents phosphorylated serine, wherein at least one of $X_1$ and $X_2$ is a positively charged amino acid and wherein n+m=1-4, wherein the formula of SEQ ID NO:1 further comprises a blocking group at the C-terminus.

9. The pharmaceutical composition of claim 8, wherein the positively charged amino acid of SEQ ID NO:1 is selected from the group consisting of lysine, arginine and histidine.

10. The pharmaceutical composition of claim 8, wherein the blocking group is selected from amid and ester.

11. The pharmaceutical composition of claim 8, wherein said composition comprises a peptide comprising the amino acid sequence set forth in any one of SEQ ID NOs 2-9 or a combination thereof.

12. The pharmaceutical composition of claim 10, wherein said composition comprises a peptide having the amino acid sequence of SEQ ID NO:12.

13. A method of inducing a transient cessation of milk production, a persistent cessation of milk production or involution in a mammary gland of a lactating mammal, comprising administering to a lactating mammal in need thereof a pharmaceutical composition comprising an effective amount of the synthetic or recombinant peptide of claim 1.

14. The method of claim 13, wherein the positively charged amino acid of SEQ ID NO: 1 is selected from the group consisting of lysine, arginine and histidine.

15. The method of claim 13, wherein the peptide of the formula of SEQ ID NO: 1, wherein the blocking group is selected from amid and ester.

16. The method of claim 13, wherein the lactating mammal is selected from a lactating livestock animal and a lactating human.

17. The method of claim 13, wherein the pharmaceutical composition is administered while the mammary gland is lactating.

18. The method of claim 13, wherein the pharmaceutical composition is administered at the same time milking or nursing is ceasing.

19. The method of claim 13, wherein the pharmaceutical composition further comprises an anti-microbial agent selected from the group consisting of antibiotic, bactericide, steroidal and non-steroidal anti-inflammatory agents, or an immunomodulator and a vaccine.

20. A method for treating or inhibiting a microbiological infection, comprising administering to a lactating animal a pharmaceutical composition comprising an effective amount of the synthetic or recombinant peptide of claim 1.

* * * * *